United States Patent [19]

Möhring et al.

[11] 4,174,392
[45] Nov. 13, 1979

[54] COMBATING ARTHROPODS WITH SUBSTITUTED TRIAZINE-2,4-DIONES

[75] Inventors: Edgar Möhring; Peter Roessler, both of Berg. Glądbach, Fed. Rep. of Germany

[73] Assignee: Bayer Aktiengesellschaft, Leverkusen, Fed. Rep. of Germany

[21] Appl. No.: 904,347

[22] Filed: May 9, 1978

[30] Foreign Application Priority Data

May 24, 1977 [DE] Fed. Rep. of Germany ....... 2723248

[51] Int. Cl.² .......................... A01N 9/00; A01N 9/22
[52] U.S. Cl. .................................... 424/249; 544/223
[58] Field of Search ......................................... 424/249

[56] References Cited

U.S. PATENT DOCUMENTS

| 4,048,315 | 9/1977 | Bredereck et al. ................. 424/249 |
| 4,068,081 | 1/1978 | Kay ..................................... 424/249 |

OTHER PUBLICATIONS

Etienne et al.; C. R. Acad. Sc. Paris, 283, 11/15/76, Series C 537 et seq.

Primary Examiner—Allen J. Robinson

Attorney, Agent, or Firm—Sprung, Felfe, Horn, Lynch & Kramer

[57] ABSTRACT

Combating arthropods with substituted triazine-2,4-diones of the formula

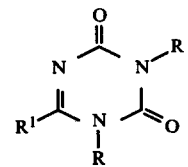

in which
R is alkyl or alkenyl with up to 20 carbon atoms, phenyl, naphthyl, or phenyl or naphthyl substituted by halogen, nitro or alkyl with 1–4 carbon atoms, and
$R^1$ is optionally substituted alkyl with 5–10 carbon atoms, or aryl.

Those compounds are new wherein
$R^1$ is optionally substituted alkyl, or is aryl when R is naphthyl, or substituted phenyl or naphthyl.

9 Claims, No Drawings

COMBATING ARTHROPODS WITH SUBSTITUTED TRIAZINE-2,4-DIONES

The present invention relates to and has for its objects the provision of new compositions for and methods of combating arthropods employing substituted triazine-2,4-diones, many of which are new, with other and further objects becoming apparent from a study of the within specification and accompanying examples.

The present invention relates to the use as arthropodicides, especially as insecticides, of certain substituted triazine-2,4-diones, some of which are known.

Certain triazine-2,4-diones and their insecticidal activity have already been disclosed (U.S. Pat. No. 4,048,315). However, their activity is not always satisfactory, especially if low concentrations are used.

Furthermore, certain triazine-2,4-diones have been disclosed by A. Etienne et al., C.R.Acad. Sc Paris, 283 (Nov. 15, 1976) Series C 537 et seq.. However, nothing has been disclosed regarding the insecticidal activity of the compounds disclosed in the said publication.

It has now been found that the substituted triazine-2,4-diones of the general formula

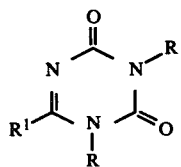

(I), in which
- R represents alkyl or alkenyl with up to 20 carbon atoms including branched and cyclic and substituted alkyl or alkenyl, or represents phenyl or naphthyl, either of which is optionally substituted by halogen, nitro or alkyl with 1–4 carbon atoms and
- $R^1$ represents alkyl with 5–10 carbon atoms, which is optionally substituted, or represents aryl, possess arthropodicidal properties, especially an excellent insecticidal activity.

Accordingly, the present invention provides an arthropodicidal composition containing as active ingredient a compound of the formula (I) in admixture with a solid or liquefied gaseous diluent or carrier or in admixture with a liquid diluent or carrier containing a surface-active agent.

The invention also provides a method of combating arthropods, especially insects, which comprises applying to the arthropods, or to a habitat thereof, a compound of the formula (I) alone or in the form of a composition containing as active ingredient a compound of the formula (I) in admixture with a diluent or carrier.

Preferably, R represents phenyl, naphthyl, m-tolyl, p-chlorophenyl, 3,4-dichlorophenyl, p-nitrophenyl, methyl, isopropyl or ω-chlorohexyl, and $R^1$ represents straight-chain or branched alkyl with 5–10 carbon atoms, cyclopentyl or cyclohexyl, which can each be substituted by halogen, $C_1$–$C_4$ alkoxy, $C_1$–$C_4$ alkylmercapto or aryloxy, or represents phenyl or naphthyl, which can each be substituted by halogen, $C_1$–$C_4$ alkyl, nitro, $C_1$–$C_4$ halogenoalkyl, $C_1$–$C_4$ alkoxy, $C_1$–$C_4$ alkylmercapto, $C_1$–$C_4$ halogenoalkoxy or $C_1$–$C_4$ halogenoalkylmercapto.

The active compounds which can be used according to the invention exhibit, coupled with favorable toxicity characteristics, a better activity than the previously known active compounds of similar structure. The new use of the active compounds according to the invention thus represents an enrichment of the art.

The present invention also provides, as new compounds, the triazine-2,4-diones of the general formula (I) in which
- $R^1$ represents alkyl with 5–10 carbon atoms, which is optionally substituted and
- R has the above-mentioned meaning and
- $R^1$ may also represent aryl provided that R represents phenyl or naphthyl which is substituted by halogen, nitro or alkyl with 1–4 carbon atoms, or represents unsubstituted naphthyl.

The compounds of the general formula (I) are obtained when (a) bis-silylated carboxylic acid amides of the general formulae

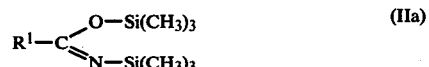

(IIa)

and

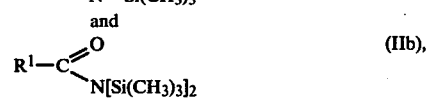

(IIb), in which
- $R^1$ has the above-mentioned meaning, are reacted with isocyanates of the general formula

in which
- R has the above-mentioned meaning, if appropriate in the presence of a diluent, or when (b) carbimic acid ethers of the general formula

(IV), in which
- $R^1$ has the above-mentioned meaning and
- $R^2$ represents alkyl with 1–4 carbon atoms or cycloalkyl, are reacted with isocyanates of the formula (III), or when (c) bis-silylated carboxylic acid amides of the general formulae (IIa) or (IIb) or carbimic acid ethers of the general formula (IV) are reacted with compounds from which the isocyanates of the formula (III) are liberated in the course of the reaction.

If bis-trimethylsilyl-benzamide and phenyl isocyanate are used as starting materials, the course of the reaction can be represented by the following equation:

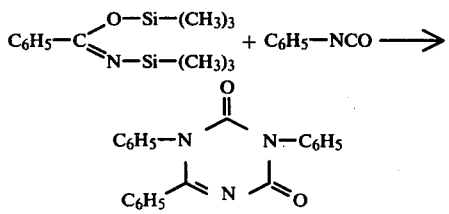

The compounds in which R represents $CH_3$, $C_2H_5$, n-$C_3H_7$ and $C_6H_5$ and $R^1$ represents $C_6H_5$ are known (A. Etienne et al., C.R. Acad.Sc. Paris, volume 283 (Nov. 15, 1976) Series C 537–540).

Particularly preferred starting compounds of the general formulea (IIa) and (IIb) are cyclohexanecarboxylic acid bis-trimethylsilylamide and bis-trimethylsilylbenzamide. The compounds of the general formulae (IIa) and (IIb) are known.

In the general formula (III), R preferably represents phenyl which can optionally be monosubstituted or polysubstituted by alkyl, chlorine or trifluoromethyl or can optionally be substituted by nitro, or represents naphthyl. Particularly preferred starting compounds of the general formula (III) are 4-chlorophenyl, 3,4-dichlorophenyl isocyanate and ω-chlorohexyl isocyanate. The compounds of the general formula (III) are known. Preferably, the isocyanates of the general formula (III) are employed in the form of compounds from which they are liberated in the course of the reaction. Uretdiones are particularly suitable for this purpose.

The reaction between the compounds (II) and (III) is preferably carried out in the presence of an inert organic diluent or solvent. As such, it is possible to use aliphatic or aromatic, optionally chlorinated, hydrocarbons, for example benzene, toluene, xylene, benzine, methylene chloride, chloroform, carbon tetrachloride and chlorobenzene; ethers, such as diethyl ether, dibutyl ether and dioxane, ketones, such as acetone, methyl ethyl ketone, ethyl isopropyl ketone and methyl isobutyl ketone; and nitriles, such as acetonitrile.

The reaction can be carried out under normal pressure.

The reaction temperature can vary within wide ranges. In general, the reaction is carried out at between 10° and 150° C., preferably between 35° and 100° C.

The starting materials are in general employed in equimolar amounts.

The following compounds of the formula (I) are particularly preferred: 1,3-bis-m,p-dichlorophenyl-6-phenyltriazine-1,4-dione, 1,3-di-p-chlorophenyl-6-phenyl-triazine-2,4-dione and 1,3-dimethyl-6-phenyl-triazine-2,4-dione.

The active compounds of the formula (I) are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and Thrips tabaci;

from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis* chrysorrhoea, Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., Pyrausta nubilalis, Ephestia kuehniella, *Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example Scorpio maurus and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

At high use concentrations, the compounds according to the invention also exhibit a certain herbicidal action.

EXAMPLE 1

Process for the preparation of 1,3-dimethyl-6-phenyltriazine-2,4-dione (Compound 1)

26.5 g (0.1 mol) of N-trimethylsilylbenzimic acid trimethylsilyl ester were added dropwise to 11.4 g (0.2 mol) of methyl isocyanate in 20 ml of absolute ether at a rate such that the solvent just boiled. After completion of the dropwise addition, the mixture was boiled for a further hour at 60° C. under reflux. The solvent and the hexamethyldisiloxane formed in the reaction were then distilled off. The residue was recrystallized from alcohol (ethanol, propanol or i-propanol).

19.4 g (89% of theory) of 1,3-dimethyl-6-phenyltriazine-2,4-dione of melting point 134°–135° C. were obtained.

The following were prepared analogously:

Table 1

$$\text{(I)} \quad \underset{R^1}{\overset{}{\mathord{\mathop{\text{N}}\limits}}}\!\!=\!\!\underset{\underset{R}{|}}{\text{N}}\!\!-\!\!\overset{\overset{O}{\|}}{\text{C}}\!\!-\!\!\text{N}\!-\!R \quad \text{with carbonyls}$$

(Structure I: a bis-acyl/amide system with substituents R, R, and R¹)

| Compound No. | R | R¹ | Melting point °C. | Yield % |
|---|---|---|---|---|
| 2 | H₃C–C₆H₄– (p-tolyl) | C₆H₅– (phenyl) | 255° | 71 |
| 3 | 1-naphthyl | C₆H₅– (phenyl) | 233° | 79 |
| 4 | C₆H₅– (phenyl) | C₆H₅– (phenyl) | 218°–219° | 92 |
| 5 | Cl–C₆H₄– (p-chlorophenyl) | C₆H₅– (phenyl) | 289° | 81 |
| 6 | 3,4-Cl₂–C₆H₃– (3,4-dichlorophenyl) | C₆H₅– (phenyl) | 282° | 89 |

The experiments given below show the arthropod-metamorphosis-inhibiting action of the compounds according to the invention, without intending to impose a limitation in respect of the breadth of action of these compounds. In these experiments, the morphological modifications, such as half-pupated animals, incompletely slipped larvae or caterpillars, defective wings and pupal cuticula of imagines, as well as the mortality, were assessed throughout the entire stated development of the test animals. The sum of the morphological malformations and of the mortality during development was recorded in percent of the number of experimental animals and the activity of the compounds was assessed from these data.

EXAMPLE 2

Metamorphosis-inhibiting action/ingestion test

Test insects: *Plutella maculipennis* (caterpillars in the 4th stage of development), 20 insects *Phaedon cochleariae* (larvae in the 4th stage of development), 20 insects Feed plants: Cabbage plants (*Brassica oleracea*)

Solvent: 10 parts by weight of dimethylformamide

Emulsifier: 1 part by weight of polyoxyethylene-sorbitan monolaurate

To produce a suitable preparation of active compound, 2 parts by weight of active compound were mixed with the stated amount of solvent and emulsifier and with sufficient water to give a 1% strength mixture which was diluted with water to the desired concentration.

The test insects were fed with leaves of the feed plants, which were provided with a uniform spray coating of the active compound mixture of the selected concentration, so that the stated amounts of active compound in ppm (parts per million) on the leaves were obtained, until the imago developed.

As a control, test insects were fed leaves which had only been treated with solvent and emulsifier of the stated concentration.

The active compounds which can be used according to the invention showed a good activity in this test.

EXAMPLE 3

Metamorphosis-inhibiting action/Laphygma test

Test insects: *Laphygma exigua* (caterpillars in the 4th stage of development)

Feed: 1 cm thick discs of 3 cm diameter of an air-dried synthetic feed of shredded beans (excluding the pods), yeast, vitamin mixture, powdered leaf, agar and preservative Solvent: 10 parts by weight of acetone Emulsifier: 1 part by weight of polyoxyethylene(20-)sorbitan monolaurate To produce a suitable preparation of active compound, 2 parts by weight of active compound were mixed with the stated amount of solvent and emulsifier and with sufficient water to give a 1% strength mixture which was diluted with water to the desired concentration.

Each test insect was placed on a separate feed disc moistened with 1.5 ml of active compound solution of the desired concentration, so that the stated concentration of active compound in ppm (parts per million) was achieved in the feed, and the insect was observed until the imago slipped. 5 to 10 test insects were used in each experiment.

As a control, test insects were each placed on a separate feed disc moistened with 1.5 ml of solvent and emulsifier of the desired concentration, so that the stated concentration in ppm (parts per million) was achieved in the feed, and each insect was observed until the imago slipped. The active compounds which can be used according to the invention showed a good activity in this test.

EXAMPLE D

Metamorphosis-inhibiting action/mosquito test

Test insects: *Aedes aegypti* (larvae in the 3rd stage of development), 20 insects Solvent: 10 parts by weight of dimethylformamide Emulsifier: 1 part by weight of polyoxyethylene(20-)sorbitan monolaurate To produce a suitable preparation of active compound, 2 parts by weight of active compound were mixed with the stated amount of solvent and emulsifier and with sufficient water to give a mixture which contained 100 ppm and which was diluted with water to the desired concentration.

The test insects were placed in 90 ml of these active compound solutions and observed until the imago slipped. As a control, test insects were introduced into a solvent and emulsifier/water mixture of the stated concentration and observed until the imago slipped.

The active compounds which can be used according to the invention showed a good activity in this test.

EXAMPLE 5

Development-inhibiting action/contact test

Test insect: *Dysdercus intermedius* (larvae in the 3rd stage of development), 10 insects Feed: cotton seeds (*Gossypium hirsutum*)
Solvent: 4 parts by weight of acetone
Emulsifier: 1 part by weight of alkylaryl polyglycol ether To produce a suitable preparation of active compound, 2 parts by weight of active compound were mixed with the stated amount of solvent and emulsifier and with sufficient water to give a 1% strength mixture which was diluted with water to the desired concentration.

The test insects were dipped for 3 seconds into the active compound mixture of the selected concentration and were then kept in cages and fed with untreated cotton seeds and water.

As a control, insects which had been dipped only in solvent and emulsifier were kept and fed in the same manner.

The active compounds which can be used according to the invention showed a good activity in this test.

It will be appreciated that the instant specification and examples are set forth by way of illustration and not limitation, and that various modifications and changes may be made without departing from the spirit and scope of the present invention.

What is claimed is:

1. A method of combating arthropods which comprises applying to the arthropods, or to a habitat thereof, an arthropodicidally effective amount of a substituted triazine-2,3-dione of the formula

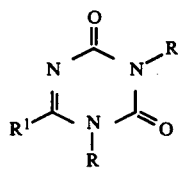

in which
R is phenyl, naphthyl, or phenyl or naphthyl substituted by halogen, nitro or alkyl with 1-4 carbon atoms, and
$R^1$ is phenyl, naphthyl, or phenyl or naphthyl substituted by halogen, $C_1$-$C_4$ alkyl, nitro, $C_1$-$C_4$ halogenalkyl, $C_1$-$C_4$ alkoxy $C_1$-$C_4$ alkylmercapto, $C_1$-$C_4$ halogenoalkoxy or $C_1$-$C_4$ halogenoalkylmercapto.

2. A method according to claim 1, in which R is phenyl, naphthyl, m-tolyl, p-chlorophenyl, 3,4-dichlorophenyl or p-nitrophenyl.

3. An arthropodicidal composition containing as active ingredient, an arthropodicidally effective amount of a substituted triazine-2,4-dione of the formula

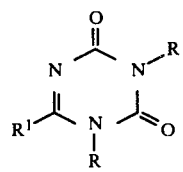

in which
R is phenyl, naphthyl, or phenyl or naphthyl substituted by halogen, nitro or alkyl with 1-4 carbon atoms, and
$R^1$ is phenyl, naphthyl, or phenyl or naphthyl substituted by halogen, $C_1$-$C_4$ alkyl, nitro, $C_1$-$C_4$ halogenoalkyl, $C_1$-$C_4$ alkoxy, $C_1$-$C_4$ alkylmercapto, $C_1$-$C_4$ halogenoalkoxy or $C_1$-$C_4$ halogenoalkylmercapto,
in admixture with a diluent.

4. A composition according to claim 3, in which the triazine-2,4-dione is
1,3-di-m-tolyl-6-phenyl-triazine-2,4-dione,
1,3-di-α-naphthyl-6-phenyl-triazine-2,4-dione,
1,3-6-triphenyl-triazine-2,4-dione,
1,3-di-p-chlorophenyl-6-phenyl-triazine-2,4-dione or
1,3-di-(3′,4′-dichlorophenyl)-6-phenyl-triazine-2,4-dione.

5. A method according to claim 1, in which said triazine-2,4-dione is 1,3-di-m-tolyl-6-phenyl-triazine-2,4-dione of the formula

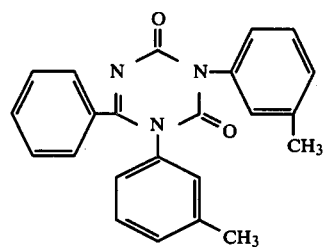

6. A method according to claim 1, in which said triazine-2,4-dione is 1,3-di-α-naphthyl-6-phenyl-triazine-2,4-dione of the formula

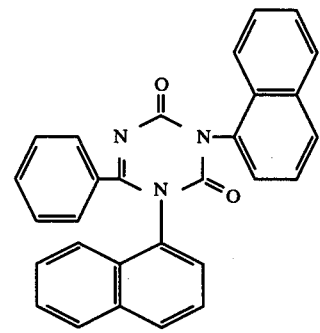

7. A method according to claim 1, in which said triazine-2,4-dione is 1,3-di-p-chlorophenyl-6-phenyl-triazine-2,4-dione of the formula

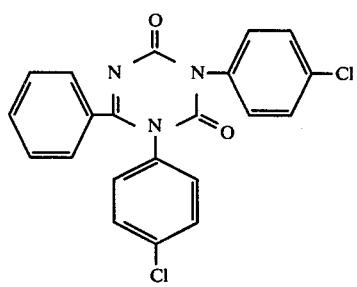

8. A method according to claim 1, in which said triazine-2,4-dione is 1,3-di-(3′,4′-dichlorophenyl)-6-phenyltriazine-2,4-dione of the formula

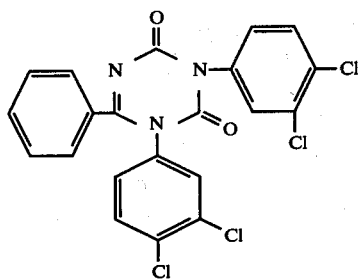
9. A method of combating arthropods which comprises applying to the arthropods, or to a habitat thereof, an arthropodicidally effective amount of 1,3-dimethyl-6-phenyl-triazine-2,4-dione of the formula
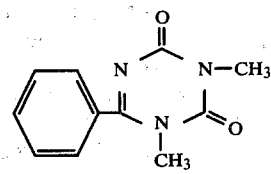
* * * * *